United States Patent [19]

Banasiak et al.

[11] Patent Number: 4,737,498
[45] Date of Patent: Apr. 12, 1988

[54] N-ALKYL-2,6-DIMETHYLMORPHOLINOCARBOXAMIDE SALTS, COMPOSITIONS AND THEIR USE AS FUNGICIDES

[75] Inventors: Lothar Banasiak; Wilfried Edlich, both of Potsdam; Horst Lyr, Eberswalde; Eva Nega; Marianne Sunkel, both of Potsdam-Babelsberg, all of German Democratic Rep.

[73] Assignee: BASF Aktiengesellschaft, Ludwigshafen, Fed. Rep. of Germany

[21] Appl. No.: 881,392

[22] Filed: Jul. 2, 1986

[30] Foreign Application Priority Data

Jul. 5, 1985 [DD] German Democratic Rep. ................................. 2783246

[51] Int. Cl.$^4$ .................... A01N 43/84; C07D 265/30
[52] U.S. Cl. .................... 514/234; 514/228; 514/232; 544/159; 544/165; 544/167; 544/268; 544/163; 71/76; 71/88
[58] Field of Search ............... 544/159, 165, 167, 168, 544/163; 514/228, 232, 234; 71/76

[56] References Cited

U.S. PATENT DOCUMENTS 4,141,718  2/1979  Martin .................................. 544/108

OTHER PUBLICATIONS

*Chem. Abst.*, vol. 104, No. 17, Apr. 28, 1986, pp. 1 and 547.

*Primary Examiner*—Robert W. Ramsuer
*Attorney, Agent, or Firm*—Keil & Weinkauf

[57] ABSTRACT

Novel N-alkyl-2,6-dimethylmorpholinocarboxamide salts of the general formula I,

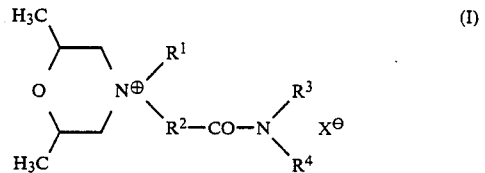

processes for their preparation, and their use as fungicides for controlling pathogenic fungi. The agents according to the invention additionally possess plant growth-regulating properties. The meanings of $R^1$, $R^2$, $R^3$, $R^4$ and $X^-$ are given in the description. (Formula I)

6 Claims, No Drawings

N-ALKYL-2,6-DIMETHYLMORPHOLINOCARBOXAMIDE SALTS, COMPOSITIONS AND THEIR USE AS FUNGICIDES

The present invention relates to novel N-alkyl-2,6-dimethylmorpholinocarboxamide salts having additional plant growth-regulating properties, and the use of these salts as fungicides in agriculture and horticulture.

It is known that N-alkylmorpholines, their salts and their molecular and addition compounds can be used as fungicides (East German Pat. No. 1,164,152 and German Pat. Nos. 1,173,722 and 2,461,513).

It is also known that quaternary ammonium compounds of long-chain N-alkyl-2,6-dimethylmorpholines having lower alkyl, alkenyl, alkoxyalkyl or aralkyl substituents possess fungicidal activity (German Pat. No. 1,167,588 and Angew. Chem. 77 (1965), 327–333). Agents which contain substituted N-benzyl- or alkoxymethyl-2,6-dimethylmorpholinium salts as active ingredients for controlling pathogenic fungi are also known (East German Pat. Nos. 134,037, 134,474 and 140,403). It is also known that morpholino-4-carboxanilides can be used for controlling phytopathogenic fungi (East German Pat. No. 141,778).

Furthermore, salts of α-aminoacetanilides which also include the morpholine ring among the amine components and have lower alkyl, cyanoalkyl, alkenyl and alkynyl substituents have been mentioned as agents for influencing or regulating plant growth (German Pat. Nos. 2,657,728 and 2,915,250).

It is also known that 2,3-dihydro-6-methyl-5-phenylcarbamyl-1,4-oxathiin 4,4-dioxide(oxycarboxin), N,N'-bis-(1-formamido-2,2,2-trichloroethyl)-piperazine(triforine) or zinc ethylene-bis-dithiocarbamate(zineb) can be used as active ingredients in fungicides for controlling fungal plant diseases (The Pesticide Manula, British Crop Protection Council; London 1979).

However, the action of the stated compounds is not always completely satisfactory for certain indications, particularly where low application rates and concentrations are used. Moreover, they show very high selectivity with respect to certain species of harmful fungi, which greatly restricts the broad use of these agents. Another disadvantage is that the toleration of these compounds by plants is not sufficient in many cases.

The aim of the present invention is to provide novel compounds which possess improved fungicidal activity and additional growth-regulating properties, a process for their preparation, and fungicides which contain such compounds, and to use such fungicides in agriculture and horticulture.

It is an object of the present invention to provide novel N-alkyl-2,6-dimethylmorpholinocarboxamide salts which possess good activity and a broad action spectrum, are very well tolerated by plants and have additional plant growth-regulating properties.

We have found that this object is achieved, and that N-alkyl-2,6-dimethylmorpholinocarboxamide salts of the general formula I

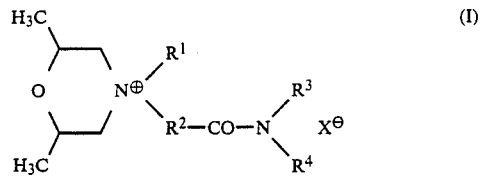

where $R^1$ is straight-chain or branched alkyl of 6 to 20 carbon atoms (for example tridecyl), $R^2$ is straight-chain or branched alkylene of 1 to 6 carbon atoms (for example methylene), $R^3$ and $R^4$ are identical or different and independently of one another are each hydrogen, straight-chain or branched alkyl of 1 to 20 carbon atoms, or straight-chain or branched alkyl of 1 to 6 carbon atoms which is substituted by hydroxyl, alkoxy of 1 to 4 carbon atoms, cyano or dialkylamino of 2 to 16 carbon atoms, or are each unsubstituted or halogen-substituted alkenyl of 3 to 6 carbon atoms, cycloalkyl of 3 to 7 carbon atoms, aryl (for example phenyl) which is monosubstituted or polysubstituted by identical or different substituents from the group consisting of straight-chain or branched alkyl of 1 to 6 carbon atoms, alkoxy of 1 to 4 carbon atoms, aryl-(lower alkyl) of 7 to 12 carbon atoms, cycloalkyl of 3 to 7 carbon atoms, acyl of 1 to 4 carbon atoms, alkoxyalkyl of 1 to 8 carbon atoms, aryl (for example phenyl), halogen, haloalkyl of 1 to 4 carbon atoms, haloalkoxy of 1 to 4 carbon atoms, alkylthio of 1 to 4 carbon atoms, haloalkylthio of 1 to 4 carbon atoms, nitro, cyano, thiocyanato, NHCOR', NHCONR'R", COOR', CONR'R", SO$_2$R' and or SO$_2$NR'R", where R' and R" independently of one another are each hydrogen, straight-chain or branched alkyl of 1 to 6 carbon atoms, cycloalkyl of 3 to 7 carbon atoms, aryl or aryl-(lower alkyl) of 7 to 12 carbon atoms, or are each aryl-(lower alkyl) of 7 to 12 carbon atoms which is monosubstituted or polysubstituted by identical or different substituents from the group consisting of straight-chain or branched alkyl of 1 to 6 carbon atoms, alkoxy of 1 to 4 carbon atoms, acyl of 1 to 4 carbon atoms, halogen, haloalkyl of 1 to 4 carbon atoms, nitro and/or cyano, or $R^3$ and $R^4$ together with the nitrogen atom form a five-membered or six-membered heterocyclic ring which is unsubstituted or monosubstituted or disubstituted by alkyl of 1 to 4 carbon atoms and/or halogen and may or may not contain one or two further hetero atoms, and X$^-$ is an anion of a non-phytotoxic acid, have a good fungicidal action. Fungicides contain, in addition to the active ingredient, the conventional solvents, carriers and/or formulation assistants. For salt formation, all organic and inorganic acids are suitable as long as they form plant-physiologically tolerated salts, e.g., chlorides, bromides, iodides, sulfates, phosphates, acetates, oxalates, fumarates, malonates, alkylsulfonates, acrylsulfonates and dodecylbenzylsulfonates.

The novel compounds can occur in two different geometric structures, ie. as N-alkyl-2,6-cis-dimethylmorpholinocarboxamide salts or N-alkyl-2,6-trans-dimethylmorpholinocarboxamide salts or as mixture of these two isomers. For use as fungicides, not only the pure isomers may be used, but also—and preferably—mixtures thereof which are obtained on synthesis. Surprisingly, we have found that the novel N-alkyl-2,6-dimethylmorpholinocarboxamide salts of the general formula I possess powerful fungicidal activity and a broad action spectrum and are particularly useful for controlling phytopathogenic fungi in crops and stored plant products. The active ingredients are well tolerated by plants at the application rates required for controlling plant diseases. The novel compounds with their growth-regulating properties can furthermore advantageously affect crops in the desired manner. We have also found that the N-alkyl-2,6-dimethylmorpholinocarboxamide salts of the general formula I are obtained if an N-alkyl-2,6-dimethylmorpholinoe of the formula II

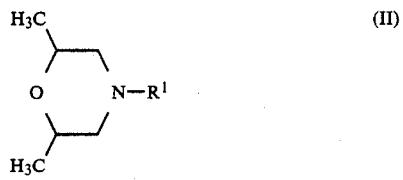

where $R^1$ has the meanings stated for the general formula I is reacted with a compound of the formula III

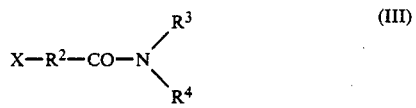

where $R^2$, $R^3$ and $R^4$ have the meanings stated for the general formula I and X is halogen, or alternatively a 2,6-dimethylmorpholinocarboxamide of the formula IV

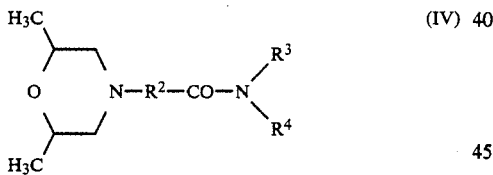

where $R^2$, $R^3$ and $R^4$ have the meanings stated for the general formula I, is reacted with a compound of the formula V

where $R^1$ has the meanings stated for the general formula I and X is halogen.

Examples of N-alkyl-2,6-dimethylmorpholines of the formula II are n-octyl, n-dodecyl-, n-tridecyl, isotridecyl-, pentadecyl- and n-didecyl-2,6-dimethylmorpholine.

Examples of halocarboxamides of the formula III are chloroacetamide, chloroacetic acid N-$C_1$-$C_{20}$-alkylamide, N-2-cyanoethylamide, N,N-diethylamide, N,N-bis-(2-cyanoethyl)-amide and N-cyclohexylamide, chloroacetanilide, chloroacetic acid 4-chloroanilide, 3,5-dichloroanilide, 3,5-dichloro-4-methoxyanilide and 1H-1,2,4-triazol-1-ylamide and 2-bromopropionic acid 3,5-dichloroanilide, 2,6-dibromo-4-nitroanilide, N-methyl-2,6-dichloro-4-cyanoanilide and 2,6-dibromo-4-thiocyanatoanilide.

Examples of 2,6-cis- and trans-dimethylmorpholino carboxamides of the formula IV are 2,6-cis- and trans-dimethylmorpholinoacetamide, 2,6-cis- and trans-dimethylmorpholinoacetic acid N-$C_1$-$C_{20}$-alkylamide, bis-(2-cyanoethyl)-amide and N-cyclohexylamide, 2,6-cis- and trans-dimethylmorpholinoacetanilide, 2,6-cis- and trans-dimethylmorpholinoacetic acid 4-chloroanilide, 3,5-dichloroanilide and 3,5-dichloro-4-methoxyanilide, and 2-(2,6-cis- and trans-dimethylmorpholino)-propionic acid 3,5-dichloroanilide, 2,6-dibromo-4-nitroanilide, 2,6-dibromo-4-thiocyanatoanilide and N-methyl-2,6-dichloro-4-cyanoanilide.

Examples of alkyl halides of the formula V are n-octyl chloride, n-dodecyl chloride, n-tridecyl chloride, isotridecyl chloride, 1,5,9-trimethyldecyl chloride, pentadecyl bromide and didecyl bromide.

The reactions to give the novel compounds of the formula I are carried out in the presence or absence of a solvent or diluent at from 10° to 180° C., preferably from 30° to 150° C. The starting materials of the formula II or of the formula IV are reacted in stoichiometric amounts with a compound of the formula III or of the formula V, respectively, or preferably with an excess of from 10 to 100%, based on the starting materials of the formula II or of the formula IV, of a compound of the formula III or of the formula V.

Examples of preferably used solvents or diluents are aliphatic or aromatic hydrocarbons and halohydrocarbons, such as n-pentane, cyclohexane, benzene, toluene, chlorobenzene, chloroform or methylene chloride, aliphatic ketones, such as acetone, methyl ethyl ketone or cyclohexanone, ethers, such as diethyl ether, tetrahydrofuran or dioxane, alcohols, such as methanol, ethanol, propanols, butanols or hexanols, nitriles, such as acetonitrile, esters, such as methyl acetate, amides, such as dimethylformamide, dimethylacetamide or N-methylpyrrolidone, dimethyl sulfoxide and water, and mixtures of these.

It is not absolutely essential to isolate the novel compounds of the general formula I from the reaction mixtures, since they may also be used for the preparation of fungicidal formulations without further purification operations.

The novel compounds of the general formula I have a powerful action against microorganisms and accordingly can be used for controlling pathogenic fungi in agriculture and horticulture. The active ingredients can be used to control undesirable fungi which occur on plants or parts of plants. The active ingredients of the general formula I are furthermore useful as dressing agents for treating seed and seedlings to protect them from fungal infections, and can be used against phytopathogenic fungi which occur in the soil. When applied, the active ingredients also have an advantageous effect on the growth processes of crop plants.

The novel active ingredients are particularly useful for preventing and curing plant diseases caused by fungi, for example *Erysiphe graminis* (powdery mildew of cereals), *Erysiphe cichoracearum* (powdery mildew of cucurbits), *Erysiphe polygoni* (powdery mildew of beans), *Podosphaera leucotricha* (powdery mildew of apple), *Sphaerotheca pannosa* (powdery mildew of roses) and *Uncinula necator* (powdery mildew of grapevines); rust diseases, such as those of the genera Puccinia, Uromyces or Hemileia, in particular *Puccinia graminis* (black rust of cereals), *Puccinia coronata* (crown rust of oats), *Puccinia sorghi* (corn rust), *Puccinia recondita* (brown leaf rust of cereals), *Uromyces fabae* (bush bean rust) and *Hemileia vastatrix* (coffee rust); *Botrytis cinerea* on grapevines and strawberries; *Monilia fructigena* on apples, *Plasmopara viticola* on grapevines; *Mycosphaerella musicola* on bananas; *Corticum salmonicolor* on Hevea; *Ganoderma pseudoferreum* on Hevea; *Exobasidium vexans* on tea; *Phytophthora infestans* on potatoes and tomatoes; and *Alternaria solani* on tomatoes. Various members of this group of active ingredients furthermore exhibit varying degrees of activity against phytopathogenic fungi, eg. *Ustilago avenae* (loose smut), *Ophiobolus graminis* (cereal foot rot), *septoria nodorum* (cereal leaf spot and glume blotch), *Venturia inaequalis* (apple scab) and various species of the genera Rhizoctonia, Tilletia, Helminthosporium, Peronospora, Pythium and Mucor.

The novel active ingredients are particularly important for controlling a large number of fungal diseases on various crops or their seeds, in particular wheat, rye, barley, oats, rice, corn, cotton, soybean, coffee, bananas, sugar cane, fruit, ornamentals in horticulture, and vegetables, such as cucumbers, beans or squash.

Because of their plant growth-regulating properties, the novel compounds can also influence the development of crops advantageously and in the desired manner. The actions of the compounds are essentially dependent on the time of application, relative to the stage of development of the seed or the plants, on the amounts of active ingredient applied to the plants or their environment, and on the method of application.

The active ingredients moreover have a good action against wood-discoloring and wood-destroying fungi, eg. *Pullaria pullulans, Aspergillus niger, Polystictus versicolor* or *Chaetomium globosum.*

The novel active ingredients of the general formula I also exhibit good activity against molds, such as Penicillium, Fusarium or Aspergillus species, which spoil agricultural products with a high moisture content or processed products obtained from agricultural products, during storage or temporary storage. Examples of products of this type to be treated include apples, oranges, mandarines, lemons, grapefruits, peanuts, cereals and cereal products, and pulse crops and ground pulses.

In addition to their broad fungicidal action spectrum, the novel active ingredients also possess varying activity against phytopathogenic bacteria, eg. Xanthomonas or Erwinia species.

Some of the active ingredients are also effective against fungi which are pathogenic in humans, eg. Trichophytes and Candida species.

Some of the active ingredients of the general formula I display a systemic action in addition to the protective action. Thus, they are absorbed via both the root and the leaves and transported into the plant tissue, or are fed to the visible parts of the plant via the seed.

The novel active ingredients are also useful for controlling resistant strains of pathogenic fungi which show signs of resistance to known fungicidal active ingredients, such as those from the group consisting of the dicarboximide fungicides, eg. 5-methyl-5-vinyl-3-(3,5-dichlorophenyl)-2,4-dioxo-1,3-oxazolidine (vinclozolin) or 5-methyl-5-methoxymethyl-3-(3,5-dichlorophenyl)-1,3-oxazolidine-2,4-dione (myclozolin); active ingredients from the group consisting of the benzimidazole or thiophanate fungicides, eg. methyl 1-(n-butylcarbamyl)-benzimidazol-2-ylcarbamate (benomyl), methyl benzimidazol-2-ylcarbamate (carbendazim) or 1,2-bis-(3-ethoxycarbonyl-2-thioureido)-benzene (thiophanate); active ingredients from the group consisting of the azole fungicides, eg. 1-(4-chlorophenoxy-3,3-dimethyl-1-(1H-1,2,4-triazol-1-yl)-butan-2-one (triadimefon) or 1-[2'-(2",4"-dichlorophenyl)-2'-(propenyloxy)-ethyl]-1,3-imidazole (imazalil); active ingredients from the group consisting of the fungicides containing aromatic hydrocarbons, eg. 2,5-dichloro-1,4-dimethoxybenzene (chloroneb) or 2,6-dichloro-4-nitroaniline (dicloran); active ingredients from the group consisting of the acylalanine fungicides, eg. methyl DL-N-(2,6-dimethylphenyl)-N-(2'-methoxyacetyl)-alanine (metalaxyl) or methyl DL-N-(2,6-dimethylphenyl)-N-(2-furoyl)-alanine (furalaxyl), and active ingredients from the group consisting of the pyrimidine fungicides, eg. 5-butyl-2-dimethylamino-4-hydroxy-6-methylpyrimidine (dimethirimol) or 2-chlorophenyl-4-chlorophenylpyrimidin-5-yl-methanol (fenarimol).

The anions $X^-$ shown in the general formula I of the novel active ingredients are not critical for the fungicidal action.

The active ingredients according to the invention can be converted to the conventional formulations, such as solutions, emulsions, wettable powders, suspensions, powders, dusting agents, foams, pastes, soluble powders, granules, natural and synthetic substances impregnated with active ingredient, very finely encapsulated forms in polymeric substances and coating compositions for seed, and ULV cold mist and warm mist formulations.

These formulations can be prepared in a conventional manner, for example by mixing or milling the novel active ingredients of the general formula I with solvents and/or carriers, with or without the use of surfactants, such as emulsifiers and/or dispersants. Suitable liquid solvents are aromatics, such as toluene, xylene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, eg. oil fractions, alcohols, such as butanols or glycols, and their esters and ethers, ketones, such as acetone, methyl ethyl ketone, methyl isobutyl ketone or cyclohexanone, highly polar solvents, such as water, dimethylformamide or dimethylsulfoxide. Liquefied solvents which are gaseous under standard conditions of temperature and pressure, for example aerosol propellants, such as halohydrocarbons, propane, butane, nitrogen and carbon dioxide, may also be employed.

Examples of suitable solid carriers are ground natural minerals, such as kaolins, clays, talc, chalk, quartz, montmorillonite or diatomaceous earth, and ground synthetic minerals, such as finely divided silica, alumina and silicates. Examples of solid carriers for granules are crushed and fractionated natural minerals, such as calcite, marble, pumice and dolomite, and synthetic granules of inorganic or organic meals, and granules of organic materials, such as sawdust, cellulose powder, powdered bark and powdered nut shells.

Examples of suitable emulsifiers are non-ionic and anionic emulsifiers, such as alkali metal, alkaline earth metal or ammonium salts of ligninsulfonic acid, naphthalenesulfonic acids, phenolsulfonic acid, alkylarylsulfonates, alkylsulfates, alkylsulfonates, alkali metal and alkaline earth metal salts of dibutylnaphthalenesulfonic acid, lauryl ether-sulfate, fatty alcohol sulfates, alkali metal and alkaline earth metal salts of fatty acids, salts of sulfated hexadecanols, heptadecanols or octadecanols, salts of sulfated fatty alcohol glycol ethers, condensates of sulfonated naphthalene and naphthalene derivatives with formaldehyde, condensates of naphthalene or of naphthalenesulfonic acids with phenol and formaldehyde, polyoxyethylene octylphenol ethers, alkylphenol polyglycol ethers, tributylphenyl polyglycol ethers, alkylaryl polyetheralcohols, isotridecyl alcohol, fatty alcohol/ethylene oxide condensates, oxyethylated castor oil, polyoxyethylene alkyl ethers, oxoethylated polyoxypropylene, lauryl alcohol polyglycol ether acetal and sorbitol esters.

Examples of suitable dispersants are ligninsulfite waste liquors and methylcellulose.

Adhesives, such as carboxymethylcellulose, natural and synthetic polymers in the form of latices, such as gum arabic, polyvinyl alcohol and polyvinyl acetate, can be used in the formulations. The formulations of the active ingredients may contain, as further additives, dyes and trace nutrients.

The formulations contain in general form 0.1 to 95, preferably from 0.5 to 90, percent by weight of active ingredient.

In the novel method for controlling fungi, an effective amount of a fungicide containing a novel active ingredient of the general formula I is allowed to act on fungi or the objects to be protected from fungal attack.

The active ingredients according to the invention, in the formulations or in the various use forms, can be mixed with other known active ingredients, such as fungicides, bactericides, insecticides, acaricides, nematicides, herbicides, growth regulators, plant nutrients and soil conditioners, and applied together with these. In many cases, mixing with fungicides give a broader fungicidal action spectrum. For a number of mixtures of the novel active ingredients with known fungicides, synergistic effects also occur, the fungicidal activity of the combination product being greater than the sum of the activities of the individual components. The following are examples of fungicides which may be combined with the novel active ingredients, although possible combinations are not restricted to these:

sulfur,
dithiocarbamates and their derivatives, such as iron(III) dimethyldithiocarbamate, zinc dimethyldithiocarbamate, manganese ethylenebisdithiocarbamate, manganese zinc ethylenediamine-bis-dithiocarbamate and zinc ethylene bisdithiocarbamate,
tetramethyl thiuramsulfides,
ammonia complex of zinc N,N-ethylene-bis-dithiocarbamate and N,N'-polyethylene-bis-(thiocarbamyl) disulfide,
ammonia complex of zinc N,N'-propylene-bis-dithiocarbamate and N,N'-propylene-bis-(thiocarbamyl) disulfide,
N-trichloromethylthio-tetrahydrophthalimide,
N-trichloromethylthio-phthalimide,
N-(1,1,2,2-tetrachloroethylthio)-tetrahydrophthalimide,
4,6-dinitro-2-(1-methylheptyl)-phenyl crotonate,
4,6-dinitro-2-sec.-butylphenyl 3,3-dimethylacrylate,
4,6-dinitro-2-sec.-butylphenyl isopropyl carbonate,
methyl 1-(n-butylcarbamyl)-benzimidazol-2-ylcarbamate,
methyl benzimidazol-2-ylcarbamate,
2-(fur-2-yl)-benzimidazole,
2-(thiazol-4-yl)-benzimidiazole,
1,2-bis-(3-methoxycarbonyl-2-thioureido)-benzene,
1,2-bis-(3-ethoxycarbonyl-2-thioureido)-benzene,
2,3-dihydro-6-methyl-5-phenylcarbamyl-1,4-oxathiin,
2,3-dihydro-6-methyl-5-phenylcarbamyl-1,4-oxathiin 4,4-dioxide,
tetrachloroisophthalodinitrile,
2,3-dichloro-1,4-naphthoquinone,
2,3-dicyano-1,4-dithioanthraquinone,
N-tridecyl-2,6-dimethylmorpholine and its salts,
N-$C_{10}$-$C_{14}$-alkyl-2,5- and/or 2,6-dimethylmorpholine,
N-cyclododecyl-2,6-dimethylmorpholine and its salts,
N-[3-p-tert.-butylphenyl)-2-methylpropyl]-2,6-cis-dimethylmorpholine and its salts,
N,N'-bis-(1-formamido-2,2,2-trichloroethyl)-piperazine,
N-(1-formamido-2,2,2-trichloroethyl)-3,4-dichloroaniline,
N-(1-formamido-2,2,2-trichloroethyl)-morpholine,
5-butyl-2-ethylamino-4-hydroxy-6-methylpyrimidine,
5-butyl-2-dimethylamino-4-hydroxy-6-methylpyrimidine,
2,4-dichlorophenyl-phenyl-pyrimidin-5-ylmethanol,
2-chlorophenyl-4-chlorophenylpyrimidin-5-ylmethanol,
bis-(4-chlorophenyl)-pyrid-3-ylmethanol,
5-methyl-5-vinyl-3-(3,5-dichlorophenyl)-1,3-oxazolidin-2,4-dione,
5-methyl-5-methoxymethyl-3-(3,5-dichlorophenyl)-1,3-oxazolidin-2,4-dione,
3-(3,5-dichlorophenyl)-N-isopropyl-2,4-dioxoimidazolidine-1-carboxamide,
N-(3,5-dichlorophenyl)-1,2-dimethylcyclopropane-1,2-dicarboximide,
1-(4-chlorophenoxy)-3,3-dimethyl-1-(1,2,4-triazol-1-yl)-butan-2-one,
1-(4-chlorophenoxy)-3,3-dimethyl-1-(1,2,4-triazol-1-yl)-butan-2-ol,
1-[2-(2,4-dichlorophenyl)-2-(propenyloxy)-ethyl]-imidazole,
1-[N-propyl-N-(2,4,6-trichlorophenoxy)-ethylcarbamyl]imidazole, 1-[2-(2,4-dichlorophenyl)-4-ethyl-1,3-dioxolan-2-ylmethyl]-1H-1,2,4-triazole,
1-[2-(2,4-dichlorophenyl)-4-n-propyl-1,3-dioxolan-2-ylmethyl]-1H-1,2,4-triazole,
1-(2,4-dichlorophenyl)-2-(1,2,4-triazol-1-yl)-4,4-dimethylpentan-3-one,
2,5-dichloro-1,4-dimethoxybenzene,
2,6-dichloro-4-nitroaniline,
diphenyl,
2-methylbenzanilide,
2-iodobenzanilide,
2,5-dimethylfuran-3-carboxanilide,
2,4,5-trimethylfuran-3-carboxanilide,
N-cyclohexyl-N-methoxy-2,5-dimethylfuran-3-carboxamide,
3-[3-(3,5-dimethyl-2-oxycyclohexyl)-2-hydroxyethyl]-glutarimide,
N-dichlorofluoromethylthio-N',N'-dimethyl-N-phenylsulfuric acid diamide,
methyl DL-N-(2,6-dimethylphenyl)-N-(2'-methoxyacetyl)-alanine,
methyl DL-N-(2,6-dimethylphenyl)-N-(2-furyl)-alanine,
N-(2,6-dimethylphenyl)-N-chloroacetyl-DL-2-aminobutyrolactone,
2,4-dichloro-6-(2-chloroanilino)-s-traizine,
O,O-diethyl phthalimido-phosphonothioate,
5-amino-1-(bis-(dimethylamino)-phosphinyl)-3-phenyl-1,2,4-triazole,
O,O-diethyl S-benzyl thiophosphate,
2-thio-1,3-dithio-(4,5-b)-quinoxaline,
4-(2-chlorophenylhydrazono)-3-methyl-5-isoxazolone,
pyridine-2-thiol 1-oxide,
8-hydroxyquinoline and its salts,
sodium 4-dimethylaminophenyldiazosulfonate,
diisopropyl 5-nitroisophthalate,
2-cyano-N-(ethylaminocarbonyl)-2-(methoxyimino)-acetamide,
2-heptadecyl-2-imidazoline acetate and
dodecylguanidine acetate.

The active ingredients can be applied as such, in the form of their formulations or the use forms prepared from these by further dilution, application being effected in a conventional manner, for example by watering, immersion, spraying, atomizing, misting, injecting, producing a suspension, painting, dusting, scattering, dry dressing, moist dressing, wet dressing, slurry dressing, or encrustation.

In the treatment of parts of plants, the concentrations of active ingredient in the use forms may be varied within a fairly wide range. They are in general from 0.0001 to 1, preferably from 0.5 to 0.001, percent by weight. The application rates for the active ingredients depend on the specific purpose and are generally from 0.1 to 3 kg or more of active ingredient per hectare.

In the treatment of seed, from 0.001 to 50 g or more, preferably from 0.01 to 10 g, of active ingredient are generally required per kilogram of seed.

For the preservation or post-harvest treatment of agricultural products or processed products obtained from agricultural products, the amounts of active ingredient required are from 0.01 to 100, preferably from 0.1 to 50, g per kilogram of material being treated.

In the treatment of the soil, active ingredients are required in concentrations of from 0.0001 to 0.1, preferably from 0.001 to 0.05, percent by weight at the place of action.

The Examples which follow illustrate the invention without restricting it, and demonstrate the action of the novel compounds of the general formula I.

ILLUSTRATIVE EXAMPLES

The Examples which follow illustrate the preparation of the novel compounds and their intermediates.

The starting compounds for the preparation of the compounds according to the invention are known per se or can be prepared by methods which are known per se, as is evident from the synthesis methods listed below.

Method for the synthesis of the halocarboxamides of the formula III:

Preparation of chloroacetic acid N,N-bis-(2-cyanoethyl-amide (intermediate for compound No. 32).

14 ml of triethylamine are added to a solution of 12.3 g of bis-(2-cyanoethyl)-amine in 100 ml of dry dioxane, after which 12.5 g (8.8 ml) of chloroacetyl chloride in 10 ml of dry dioxane are added dropwise in the course of 1 hour. During this procedure, the temperature is kept below 30° C. The reaction mixture is stirred for 2 hours at room temperature and then poured onto 200 ml of ice water. The product is extracted with ethyl acetate, and the organic phase is washed with water, dried over sodium sulfate and evaporated down under reduced pressure. The crude product is recrystallized from acetone/n-hexane. Yield: 14 g. Mp. 68°–68.5° C.

Method for the synthesis of the 2,6-cis- and/or trans-dimethylmorpholinocarboxamides of the formula IV:

Preparation of 2-(2,6-cis- and/or trans-dimethylmorpholino)-propionic acid 3,5-dichloroanilide (intermediate for compound No. 80).

22.6 g of 2,6-cis-dimethylmorpholine are dissolved in 100 ml of dry dioxane, and a solution of 29.7 g of 2-bromopropionic acid 3,3-dichloroanilide in 20 ml of dry dioxane is added dropwise. The reaction mixture is then refluxed for 3 hours and evaporated to dryness under reduced pressure. The product is recrystallized from methanol. Yield: 26 g. Mp. 158°–158.8° C.

EXAMPLE 1

N-Isotridecyl-2,6-cis- and/or trans-dimethylmorpholinoacetic acid N',N'-bis-(2-cyanoethyl)-amide chloride 30 g of N-isotridecyl-2,6-cis- and/or trans-dimethylmorpholine and 20 g of chloroacetic acid N,N-di-(2-cyanoethyl)-amide in 100 ml of acetonitrile are refluxed for 24 hours, with the addition of a catalytic amount of sodium iodide. The mixture is cooled, the solvent is distilled off under reduced pressure, the product is dissolved in a little diethyl ether, and n-hexane is added until precipitation is complete. Evaporation under reduced pressure gives 45 g of a yellowish brown viscous oil (compound No. 32).

IR spectrum (film): C=O—absorption 1660 cm$^{-1}$.

EXAMPLE 2

2-N-Isotridecyl-2,6-cis- and/or trans-dimethylmorpholino)-propionic acid 3,5-dichloroanilide bromide 30 g of N-isotridecyl-2,6-cis- and/or trans-dimethylmorpholine and 29.8 g of 2-bromopropionic acid 3,5-dichloroanilide in 100 ml of n-butanol are refluxed for 24 hours, with the addition of a catalytic amount of sodium iodide. The mixture is cooled, the solvent is distilled off under reduced pressure, the product which remains is dissolved in a little diethyl ether, and n-hexane is added until precipitation is complete. The oily phase is evaporated and freed from residual solvent under reduced pressure. 54 g of a yellowish brown, highly viscous oil are obtained (compound No. 80).

IR spectrum (film): C=O—absorption 1690 cm$^{-1}$.

EXAMPLE 3

N-Isotridecyl-2,6-cis- and/or trans-dimethylmorpholinoacetic acid 3,4-dichloroanilide chloride 31.7 g of 2,6-cis- and/or trans-dimethylmorpholinoacetic acid 3,4-dichloroanilide and 21.9 g of isotridecyl chloride (mixture of various $C_{11}$–$C_{14}$-alkyl chlorides which contains from 60 to 70% of n-tridecyl chloride) in 100 ml of dimethylformamide are refluxed for 12 hours. After the mixture has cooled, the solvent is distilled off under reduced pressure, the crude product is dissolved in a little diethyl ether, and n-hexane is added until precipitation is complete. The oily phase is separated off and freed from residual solvent under reduced pressure. 48 g of a pale brown resin are obtained (compound No. 75).

IR spectrum (film): C=O—absorption 1690 cm$^{-1}$.

A similar procedure is used to prepare the compounds of the general formula I which are listed below and which as a rule are yellow to brown viscous oils or resins, are readily soluble in polar solvents, such as alcohols, acetone, dimethylformamide or dimethyl sulfoxide, and have the characteristic absorption bands of the carbonyl group in the IR spectrum.

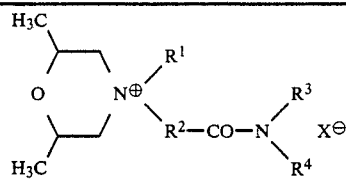
(I)

| No. | R$^1$ | R$^2$ | R$^3$ | R$^4$ | X |
|---|---|---|---|---|---|
| 1 | n-hexyl | CH$_2$ | H | H | Cl |
| 2 | n-octyl | CH$_2$ | H | H | Cl |
| 3 | n-decyl | CH$_2$ | H | H | Cl |
| 4 | n-dodecyl | CH$_2$ | H | H | Cl |
| 5 | n-tridecyl | CH$_2$ | H | H | Cl |
| 6 | 1,5,9-trimethyldecyl | CH$_2$ | H | H | Cl |
| 7 | isotridecyl | CH$_2$ | H | H | Cl |
| 8 | isotridecyl | CH$_2$ | H | methyl | Cl |
| 9 | isotridecyl | CH$_2$ | H | ethyl | Cl |
| 10 | isotridecyl | CH$_2$ | H | sec-butyl | Cl |
| 11 | isotridecyl | CH$_2$ | H | 2-ethylhexyl | Cl |
| 12 | isotridecyl | CH$_2$ | H | n-dodecyl | Cl |
| 13 | isotridecyl | CH$_2$ | H | n-octadecyl | Cl |
| 14 | isotridecyl | CH$_2$ | H | 3-hydroxypropyl | Cl |
| 15 | isotridecyl | CH$_2$ | H | 3-ethoxypropyl | Cl |
| 16 | isotridecyl | CH$_2$ | H | 2-cyanoethyl | Cl |
| 17 | isotridecyl | CH$_2$ | H | 2-diethylaminoethyl | Cl |
| 18 | isotridecyl | CH(CH$_3$) | H | H | Br |
| 19 | isotridecyl | CH(CH$_3$) | H | n-dodecyl | Br |
| 20 | isotridecyl | CH(C$_2$H$_5$) | H | n-butyl | Br |
| 21 | isotridecyl | C(CH$_3$)$_2$ | H | n-butyl | Br |
| 22 | isotridecyl | CH(C$_5$H$_{11}$) | H | n-butyl | Br |
| 23 | isotridecyl | (CH$_2$)$_3$ | H | n-butyl | Cl |
| 24 | isotridecyl | (CH$_2$)$_6$ | H | n-butyl | Br |
| 25 | n-C$_{15}$H$_{31}$ | CH$_2$ | H | n-butyl | Cl |
| 26 | n-C$_{20}$H$_{41}$ | CH$_2$ | H | n-butyl | Cl |
| 27 | isotridecyl | CH$_2$ | ethyl | ethyl | Cl |
| 28 | isotridecyl | CH$_2$ | n-octyl | n-octyl | Cl |
| 29 | isotridecyl | CH(CH$_3$) | n-butyl | n-butyl | Br |
| 30 | isotridecyl | CH$_2$ | 2-hydroxyethyl | 2-hydroxyethyl | Cl |
| 31 | n-octyl | CH$_2$ | 2-cyanoethyl | 2-cyanoethyl | Cl |
| 32 | isotridecyl | CH$_2$ | 2-cyanoethyl | 2-cyanoethyl | Cl |
| 33 | isotridecyl | CH$_2$ | methyl | 3-cyanopropyl | Cl |
| 34 | isotridecyl | CH$_2$ | H | allyl | Cl |
| 35 | isotridecyl | CH(CH$_3$) | allyl | allyl | Br |
| 36 | isotridecyl | CH$_2$ | methyl | crotyl | Cl |
| 37 | isotridecyl | CH$_2$ | methyl | 4-chlorobut-2-en-1-yl | Cl |
| 38 | isotridecyl | CH$_2$ | methyl | propargyl | Cl |
| 39 | isotridecyl | CH$_2$ | H | cyclopropyl | Cl |
| 40 | isotridecyl | CH(CH$_3$) | H | cyclopentyl | Br |

-continued

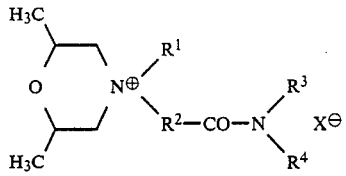 (I)

| No. | R¹ | R² | R³ | R⁴ | X |
|---|---|---|---|---|---|
| 41 | isotridecyl | CH(CH₃) | H | cyclohexyl | Br |
| 42 | isotridecyl | CH₂ | H | cycloheptyl | Cl |
| 43 | isotridecyl | CH₂ | ethyl | cyclohexyl | Cl |
| 44 | isotridecyl | CH₂ | H | phenyl | Cl |
| 45 | isotridecyl | CH₂ | methyl | phenyl | Cl |
| 46 | isotridecyl | CH₂ | n-propyl | phenyl | Cl |
| 47 | isotridecyl | CH₂ | allyl | phenyl | Cl |
| 48 | isotridecyl | CH₂ | propargyl | phenyl | Cl |
| 49 | isotridecyl | CH₂ | benzyl | phenyl | Cl |
| 50 | isotridecyl | CH(CH₃) | alyil | phenyl | Br |
| 51 | isotridecyl | CH₂ | H | naphth-1-yl | Cl |
| 52 | isotridecyl | CH₂ | H | biphen-2-yl | Cl |
| 53 | isotridecyl | CH₂ | H | 2-chlorophenyl | Cl |
| 54 | isotridecyl | CH₂ | H | 3-fluorophenyl | Cl |
| 55 | isotridecyl | CH₂ | H | 4-chlorophenyl | Cl |
| 56 | isotridecyl | CH(CH₃) | methyl | 3-bromophenyl | Br |
| 57 | isotridecyl | CH₂ | H | 4-ethylphenyl | Cl |
| 58 | isotridecyl | CH(CH₃) | methyl | 4-n-butoxyphenyl | Br |
| 59 | isotridecyl | CH(CH₃) | methyl | 4-formylphenyl | Br |
| 60 | isotridecyl | CH(CH₃) | methyl | 4-acetophenyl | Br |
| 61 | isotridecyl | CH₂ | H | 3-nitrophenyl | Cl |
| 62 | isotridecyl | CH₂ | H | 4-cyanophenyl | Cl |
| 63 | isotridecyl | CH₂ | H | 3-trifluoromethylphenyl | Cl |
| 64 | isotridecyl | CH₂ | H | 4-thiocyanatophenyl | Cl |
| 65 | isotridecyl | CH₂ | H | 4-acetaminophenyl | Cl |
| 66 | isotridecyl | CH₂ | H | 4-methoxycarbonylphenyl | Cl |
| 67 | isotridecyl | CH₂ | H | 4-N,N—dimethylamidocarbonylphenyl | Cl |
| 68 | isotridecyl | CH₂ | H | 4-N,N—dimethylureidophenyl | Cl |
| 69 | isotridecyl | CH₂ | H | 4-N,N—dimethylamidosulfenylphenyl | Cl |
| 70 | isotridecyl | CH₂ | H | 4-phenylsulfonylphenyl | Cl |
| 71 | isotridecyl | CH₂ | H | 2,3-dichlorophenyl | Cl |
| 72 | isotridecyl | CH₂ | H | 2,4-dichlorophenyl | Cl |
| 73 | isotridecyl | CH₂ | H | 2,5-dichlorophenyl | Cl |
| 74 | isotridecyl | CH₂ | H | 2,6-dibromophenyl | Cl |
| 75 | isotridecyl | CH₂ | H | 3,4-dichlorophenyl | Cl |
| 76 | n-octyl | CH₂ | H | 3,5-dichlorophenyl | Cl |
| 77 | n-octyl | CH₂ | methyl | 3,5-dichlorophenyl | Cl |
| 78 | n-octyl | CH(CH₃) | H | 3,5-dichlorophenyl | Br |
| 79 | isotridecyl | CH₂ | H | 3,5-dichlorophenyl | Cl |
| 80 | isotridecyl | CH(CH₃) | H | 3,5-dichlorophenyl | Br |
| 81 | isotridecyl | CH(CH₃) | methyl | 3,5-dichlorophenyl | Br |
| 82 | isotridecyl | CH(CH₃) | allyl | 3,5-dichlorophenyl | Br |
| 83 | isotridecyl | CH₂ | H | 3,5-dibromophenyl | Cl |
| 84 | isotridecyl | CH(CH₃) | H | 3,5-dibromophenyl | Br |
| 85 | isotridecyl | CH(CH₃) | methyl | 3,5-dibromophenyl | Br |
| 86 | isotridecyl | CH₂ | H | 2,6-diethylphenyl | Cl |
| 87 | isotridecyl | CH₂ | H | 3,4-dimethylphenyl | Cl |
| 88 | isotridecyl | CH₂ | H | 3,5-dimethylphenyl | Cl |
| 89 | isotridecyl | CH₂ | H | 2-nitro-4-trifluoromethylphenyl | Cl |
| 90 | isotridecyl | CH₂ | H | 2-methyl-4-chlorophenyl | Cl |
| 91 | isotridecyl | CH(CH₃) | H | 2-methyl-4-chlorophenyl | Br |
| 92 | isotridecyl | CH₂ | H | 2-cyano-4-nitrophenyl | Cl |
| 93 | isotridecyl | CH₂ | H | 3,5-dinitrophenyl | Cl |
| 94 | isotridecyl | CH₂ | H | 2,6-dibromo-4-nitrophenyl | Cl |
| 95 | isotridecyl | CH₂ | methyl | 2,6-dibromo-4-nitrophenyl | Cl |
| 96 | isotridecyl | CH(CH₃) | H | 2,6-dibromo-4-nitrophenyl | Br |
| 97 | isotridecyl | CH(CH₃) | methyl | 2,6-dibromo-4-nitrophenyl | Br |
| 98 | isotridecyl | CH₂ | H | 2,6-dichloro-4-cyanophenyl | Cl |
| 99 | isotridecyl | CH₂ | methyl | 2,6-dichloro-4-cyanophenyl | Cl |
| 100 | isotridecyl | CH(CH₃) | H | 2,6-dichloro-4-cyanophenyl | Br |
| 101 | isotridecyl | CH(CH₃) | methyl | 2,6-dichloro-4-cyanophenyl | Br |
| 102 | isotridecyl | CH₂ | H | 3,4,5-trichloro-phenyl | Cl |
| 103 | isotridecyl | CH₂ | methyl | 3,4,5-trichloro-phenyl | Cl |
| 104 | isotridecyl | CH₂ | H | 2,4,6-trichloro-phenyl | Cl |
| 105 | isotridecyl | CH₂ | methyl | 2,4,6-trichloro-phenyl | Cl |
| 106 | isotridecyl | CH₂ | H | 2,6-dibromo-4-thiocyanatophenyl | Cl |
| 107 | isotridecyl | CH₂ | methyl | 2,6-dibromo-4-thiocyanatophenyl | Cl |
| 108 | isotridecyl | CH(CH₃) | H | 2,6-dibromo-4-thiocyanatophenyl | Br |
| 109 | isotridecyl | CH(CH₃) | methyl | 2,6-dibromo-4-thiocyanatophenyl | Br |
| 110 | isotridecyl | CH₂ | H | 3,5-dichloro-4-methoxyphenyl | Cl |
| 111 | isotridecyl | CH₂ | methyl | 3,5-dichloro-4-methoxyphenyl | Cl |
| 112 | isotridecyl | CH(CH₃) | H | 3,5-dichloro-4-methoxyphenyl | Br |

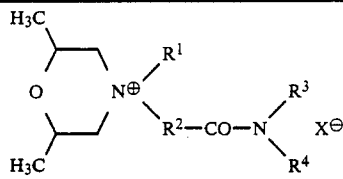

(I)

| No. | R¹ | R² | R³ | R⁴ | X |
|---|---|---|---|---|---|
| 113 | isotridecyl | CH(CH₃) | methyl | 3,5-dichloro-4-methoxyphenyl | Br |
| 114 | isotridecyl | CH₂ | H | benzyl | Cl |
| 115 | isotridecyl | CH(CH₃) | H | phenethyl | Br |
| 116 | isotridecyl | CH(CH₃) | methyl | 4-chlorobenzyl | Br |
| 117 | isotridecyl | CH₂ | H | 4-methylbenzyl | Cl |
| 118 | isotridecyl | CH₂ | H | 4-tert-butylbenzyl | Cl |
| 119 | isotridecyl | CH₂ | H | 4-methoxybenzyl | Cl |
| 120 | isotridecyl | CH₂ | H | 3-trifluoromethylbenzyl | Cl |
| 121 | isotridecyl | CH₂ | methyl | 4-cyanobenzyl | Cl |
| 122 | isotridecyl | CH(CH₃) | H | 4-nitrobenzyl | Br |
| 123 | isotridecyl | CH₂ | H | 3,4-dichlorobenzyl | Cl |
| 124 | isotridecyl | CH₂ | H | 2,3,4-trichlorobenzyl | Cl |
| 125 | isotridecyl | CH₂ | aziridin-1-yl | | Cl |
| 126 | isotridecyl | CH₂ | pyrrol-1-yl | | Cl |
| 127 | isotridecyl | CH₂ | pyrrolidin-1-yl | | Cl |
| 128 | isotridecyl | CH₂ | pyrazol-1-yl | | Cl |
| 129 | isotridecyl | CH₂ | 1H—imidazol-1-yl | | Cl |
| 130 | isotridecyl | CH₂ | 1H—1,2,4-triazol-1-yl | | Cl |
| 131 | isotridecyl | CH₂ | piperidin-1-yl | | Cl |
| 132 | isotridecyl | CH₂ | 3,5-dimethylpiperidin-1-yl | | Cl |
| 133 | isotridecyl | CH₂ | 4-methylpiperazin-1-yl | | Cl |
| 134 | isotridecyl | CH(CH₃) | tetrahydro-1,4-oxazin-4-yl | | Br |
| 135 | isotridecyl | CH(CH₃) | 2,6-cis/trans-dimethyl-tetrahydro-1,4-oxazin-4-yl | | Br |
| 136 | isotridecyl | CH(CH₃) | tetrahydro-1,4-thiazin-4-yl | | Br |
| 137 | isotridecyl | CH(CH₃) | 2,6-cis/trans-dimethyl-tetrahydro-1,4-diazin-4-yl | | Br |
| 138 | isotridecyl | CH₂ | oxazolidin-3-yl | | Cl |
| 139 | isotridecyl | CH₂ | thiazolidin-3-yl | | Cl |

| Compound no. | IR spectra (film) cm⁻¹ |
|---|---|
| 7 | 3360 ... 3220, 3170 ... 3130, 2960 ... 2900, 2810, 1675, 1620, 1550, 1370, 1135, 1105, 1025 |
| 16 | 3370 ... 3330, 3190, 3020, 2955, 2925, 2865, 1680, 1555, 1455, 1420, 1380, 1240, 1140, 1025 |
| 27 | 3390 ... 3310, 2970 ... 2910, 2875, 1650, 1460, 1380, 1145, 1115 |
| 31 | 3350 ... 3310, 2960 ... 2900, 2850, 2240, 1650, 1450, 1365, 1145, 1100, 1060, 1015 |
| 32 | 3390 ... 3330, 2960, 2940, 2880, 2250, 1660, 1470, 1420, 1140, 1035 |
| 44 | 3370 ... 3300, 3265, 3190, 3130, 2980 ... 2900, 2860, 1685, 1600, 1555, 1500, 1455, 1375, 1315, 1145 |
| 55 | 3390 ... 3340, 3220, 3170, 3105, 3015, 2955, 2930, 2870, 1690, 1610, 1550, 1490, 1460, 1395, 1375, 1305, 1245, 1210, 1140, 1090, 1010, 830 |
| 72 | 3390 ... 3370, 3185, 3140, 2970 ... 2920, 2875, 2460, 1700, 1595, 1540, 1490, 1480, 1395, 1300, 1250, 1225, 1155, 1110, 1070, 875, 830 |
| 75 | 3400 ... 3450, 3220, 3150, 3070, 2950, 2920, 2860, 1690, 1585, 1530, 1465, 1370, 1295, 1230, 1125, 1020, 870, 810 |
| 76 | 3380 ... 3340, 3220, 3150, 3090, 3080, 2970 ... 2890, 2860, 1680, 1580, 1540, 1430, 1400, 1360, 1295, 1250, 1195, 1135, 1100, 1010, 830, 790 |
| 79 | 3395 ... 3360, 3225, 3165, 3105, 3025, 2960, 2940, 2870, 1695, 1590, 1550, 1445, 1410, 1375, 1310, 1270, 1210, 1145, 1115, 1035, 875, 845, 805 |
| 80 | 3370 ... 3210, 3200, 3165, 3105, 3075, 3045, 2960, 2925, 2870, 2615, 1690, 1585, 1533, 1440, 1405, 1370, 1155, 1110, 1085 |
| 83 | 3390 ... 3350, 3220, 3155, 2960, 2930, 2870, 1695, 1583, 1535, 1435, 1405, 1380, 1300, 1260, 1215, 1140, 1105, 870, 855 |
| 84 | 3360 ... 3210, 3145, 3095, 3070, 2970 ... 2910, 2865, 2620, 1695, 1585, 1525, 1470, 1425, 1405, 1380, 1300, 1255, 1180, 1160, 1115, 1085, 840 |
| 86 | 3360 ... 3240, 3165, 2955, 2920, 2865, 1675, 1580, 1520, 1450, 1370, 1315, 1260, 1220, 1130, 1025, 865 |
| 94 | 3400 ... 3360, 3310 ... 3260, 2960, 2930, 2860, 1695, 1595, 1540, 1520, 1470, 1380, 1350, 1210, 1140, 725 |
| 106 | 2970 ... 2900, 2850, 2160, 1690, 1570, 1470, 1380, 1210, 1140, 725 |
| 114 | 3400 ... 3180, 3065, 3035, 2965, 2935, 2875, 1680, 1610, 1535, 1470, 1460, 1385, 1150, 1120, 1085, 1035, 875 |

The novel compounds of the general formula I can be used in the form of, for example, the following formulations:

EXAMPLE I

Solution concentrates: 80 parts by weight of compound 7 are mixed with 20 parts by weight of N-methyl-2-pyrrolidone. A solution suitable for use in the form of very small droplets is obtained.

EXAMPLE II

Emulsifiable concentrates: 25 parts by weight of compound 55 are mixed with 2.5 parts by weight of epoxidized vegetable oil, 10 parts by weight of an alkylarylsulfonate/fatty alcohol polyglycol ether mixture, 5 parts by weight of dimethylformamide and 57.5 parts by weight of xylene. Emulsions of any desired concentration may be prepared from this concentrate by dilution with water.

EXAMPLE III

Wettable powder: 40 parts by weight of compound 86 are mixed thoroughly with 5 parts by weight of the sodium salt of a ligninsulfonic acid from a sulfite waste liquor, 1 part by weight of sodium diisobutylnaphthalenesulfonate and 54 parts by weight of silica gel, and the mixture is milled in an appropriate mill. A wettable powder which can be diluted with water to give suspensions of any desired concentration is obtained.

EXAMPLE IV

Dusting agent: 5 parts by weight of compound 80 are mixed thoroughly with 95 parts by weight of finely divided kaolin, and the mixture is milled. The dusting agents can be used in this form for dusting.

EXAMPLE V

Granules: 5 parts by weight of compound 86 are mixed with 0.25 parts by weight of epichlorohydrin, and the mixture is dissolved in 6 parts by weight of acetone. 3.5 parts by weight of polyethylene glycol and 0.25 part by weight of cetyl polyglycol ether are then added. The resulting solution is sprayed onto kaolin and the acetone is then evaporated under reduced pressure to give microgranules in a form suitable for use.

The Examples which follow illustrate the invention without restricting it, and demonstrate the action of the compounds of the general formula I.

EXAMPLE A

Mycelium growth test

The fungicidal action of the agents on the test fungi is determined in a conventional manner, as the inhibition of the radial mycelium growth on a malt agar nutrient medium (2% of malt) in Petri dishes of 9 cm diameter at an incubation temperature of 25° C. To do this, the active ingredients are dissolved in dimethylformamide, and the solution is diluted with water and mixed with the liquid agar so that the desired concentration of active ingredient in the nutrient medium is obtained. The dimethylformamide content must not exceed 0.5% by volume. After cooling, the plates are inoculated. Evaluation is carried out when the controls without added ingredient show a growth corresponding to 70–90% of the dish diameter, the time at which evaluation is effected depending on the rate of growth of the fungi. Evaluation involves calculating the inhibition of growth, in percent, produced by the active ingredients, in comparison with the controls without added active ingredient (Table A).

TABLE A

| | | Inhibition of growth of fungi in the mycelium growth test | |
|---|---|---|---|
| | | Inhibition of growth in percent | |
| Compound No. | Concentration of active ingredient | Botrytis cinerea 10 μg/ml | Phytophthora cactorum 50 μg/ml |
| Oxycarboxin (known) | | 20 | 50 |
| 7 | | 57 | |
| 16 | | 36 | 72 |
| 27 | | 83 | |
| 31 | | 43 | |
| 32 | | 71 | |
| 41 | | 62 | |
| 44 | | 89 | 110 |
| 55 | | 77 | 93 |
| 72 | | 74 | |
| 75 | | 76 | 65 |
| 79 | | 74 | 70 |
| 80 | | 80 | |
| 83 | | 58 | |
| 84 | | 69 | 56 |
| 86 | | 63 | |
| 94 | | 82 | |
| 114 | | 43 | |
| 129 | | 71 | |
| 130 | | 88 | |

EXAMPLE B

Barley powdery mildew test (*Erysiphe graminis*/barley)

In tubes containing sand, barley plants of the Astacus variety at the 1-leaf stage are sprayed, until dew-moist, with formulations of active ingredients which are prepared from 1 part by weight of active ingredient, 100 parts by weight of dimethylformamide and 0.25 part by weight of an alkylaryl polyglycol-ether and diluted with water to the desired concentration of active ingredient. After the spray coating has dried on, the plants are dusted with conidia of powdery mildew of barley (*Erysiphe graminis* var. *hordei*). The test plants are then placed in an incubation cabin for from 2 to 3 hours at from 90 to 100% relative humidity, after which they are placed in a greenhouse at from 20° to 22° C. and from 75 to 80% relative humidity.

After 7 days, the infestation of the barley plants by powdery mildew is determined. The ratings obtained according to STEPHAN (Arch. Phytopath. Pfl.-schutz 14 (1978), 163–175) are converted to the degree of infestation according to KRUGER (Nachr.-Bl. Pflanzenschutz DDR 1981, 145–147). From these, the efficiency (E) according to ABBOTT is obtained as follows:

$$E \text{ (in \%)} = \frac{\text{Degree of infestation of control} - \text{degree of infestation of variant}}{\text{degree of infestation of control}} \times 100$$

The results are shown in Table B.

TABLE B

| Action against *Erysiphe graminis* on barley Concentration of active ingredient: 10 mg/l | |
|---|---|
| Compound No. | Efficiency in percent |
| N—Methyl-N—tridecyl-2,6-dimethyl-morpholinium methosulfate (disclosed in German Patent 1,167,588) | 82 |
| Triforine (known) | 86 |
| 7 | 87 |
| 32 | 94 |
| 75 | 82 |
| 94 | 92 |
| 130 | 96 |

EXAMPLE C

Cereal rust test (*Puccinia recondita*/wheat)

Wheat plants of the Alcedo variety grown in pots are cut back to a height of 12 cm at the two-leaf stage. The secondary leaf of the plants is removed. The wheat plants are then sprayed with formulations of active ingredients which are prepared from 20 parts by weight of active ingredient, 10 parts by weight of polyoxyethylene sorbitan monostearate (Tween 60), 5 parts by weight of polypropyleneglycol, 25 parts by weight of cyclohexanone and 40 parts by weight of toluene and diluted with water to the desired concentration of active ingredient. After the spray coating has dried on, the plants are inoculated with spores of wheat brown rust (*Puccinia recondita*), which are applied as a suspension in water, with the addition of Tween 60. The test plants are then placed in a water vapor-saturated incubation cabin for 24 hours, after which they are placed in a greenhouse at from 20° to 22° C. and from 70 to 80% relative humidity. After 10 days, the infestation of the wheat plants by rust is determined.

The efficiency of the agents is determined by the method described in Example B.

The results are shown in Table C.

TABLE C

Action against *Puccinia recondita* on wheat
Concentration of active ingredient: 500 mg/l

| Compound No. | Efficiency in percent |
| --- | --- |
| Triforine (known) | 64 |
| 79 | 83 |
| 80 | 85 |
| 86 | 76 |

EXAMPLE D

Botrytis test (*Botrytis cinerea*/field bean (*Vicia faba*) Leaflets

Leaflets cut from field bean plants (*Vicia fabia*) of the Fribo variety, which have been grown in pots and are at the four-leaf stage, are painted with formulations of active ingredients which are prepared from 1 part by weight of active ingredient, 100 parts by weight of dimethylformamide and 0.25 part by weight of alkylaryl polyglycol ether and diluted with water to the desired concentration of active ingredient. When the spray coating has dried on, the leaves are inoculated with a conidia suspension of *Botrytis cinerea*, obtained by washing from 12 to 16 day-old fungus cultures from malt agar nutrient medium (2% of malt). The field bean leaflets are kept in dishes in an incubation cabin at 22° C. and from 90 to 100% relative humidity.

After 4 days, the infestation of the field bean leaflets by Botrytis is determined. The percentage infestation based on the entire leaf area is converted into the efficiency of the agents, according to ABBOTT. The results are shown in Table D.

TABLE D

Action against *Botrytis cinerea* on field bean (*Vicia faba*) leaflets
Concentration of active ingredient: 100 mg/l

| Compound No. | Efficiency in percent |
| --- | --- |
| Tridemorph (known) | 42 |
| 76 | 74 |
| 79 | 47 |
| 86 | 45 |

EXAMPLE E

Phytophthora test (*Phytophthora infestans*/tomato)

Tomato plants of the Tamina variety which have been grown in pots and are at the three-leaf stage are sprayed, until dew-moist, with formulations of active ingredients which are prepared from 1 part by weight of active ingredient, 100 parts by weight of dimethylformamide and 0.25 part by weight of alkylaryl polyglycol ether and diluted with water to the desired concentration of active ingredient. When the spray coating has dried on, the tomato plants are inoculated with an aqueous zoospore suspension of *Phytophthora infestans*. The test plants are then placed in an incubation chamber at from 18° to 20° C. and from 95 to 100% relative humidity.

After 5 days, the infestation of the tomato plants by Phytophthora is determined. The ratings obtained are converted to the degree of infestation and the efficiency of the agents, as described in Example B.

The results are shown in Table E.

TABLE E

Action against *Phytophthora infestans* on tomatoes

| Compound No. | Concentration of active ingredient in mg/l | Efficiency in percent |
| --- | --- | --- |
| Zineb (known) | 100 | 57 |
|  | 200 | 61 |
| 79 | 100 | 60 |
|  | 200 | 77 |

EXAMPLE F

Plant growth regulation test

Cucumber plants of the Eva variety are grown in pots in a greenhouse, in humus which is adequately supplied with nutrients, until a height of growth of 9 cm is reached. 10 plants per test variant are used. The cucumber plants are sprayed with formulations of active ingredients which are prepared from 1 part by weight of active ingredient, 100 parts by weight of dimethylformamide and 0.25 part by weight of alkylarylpolyglycol ether and diluted with water to the desired concentration of active ingredient.

After a growth period of 14 days after the application of the agent, the lengths of the treated plants and of the untreated control plants are measured.

The results are shown in Table F.

TABLE F

Action on the length of growth of cucumber plants on leaf treatment
Concentration of active ingredient 1000 mg/l

| Compound No. | Plant height in cm | relative |
| --- | --- | --- |
| Untreated control | 26.5 | 100 |
| 79 | 21.0 | 79.5 |

We claim:

1. An N-alkyl-2,6-dimethylmorpholinocarboxamide salt of the formula I

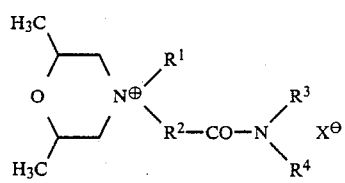

where $R^1$ is straight-chain or branched alkyl of 6 to 20 carbon atoms, $R^2$ is straight-chain or branched alkylene of 1 to 6 carbon atoms, $R^3$ is hydrogen or alkyl of 1 to 3 carbon atoms, $R^4$ is dihalophenyl or $C_1$ to $C_6$ dialkylphenyl, and $X^-$ is an anion of a non-phytotoxic acid.

2. An N-alkyl-2,6-dimethylmorpholinocarboxamide salt as claimed in claim 1, wherein $R^1$ is isotridecyl, $R^2$ is —$CH_2$—, $R^3$ is hydrogen, $R^4$ is 3,5-dichlorophenyl or 3,5-dibromophenyl and $X^-$ is chloride or bromide.

3. 2-(N-Isotridecyl-2,6-dimethylmorpholino)-acetic acid 3,5-dichloroanilide chloride.

4. 2-(N-Isotridecyl)-2,6-dimethylmorpholino)-acetic acid 3,5-dibromoanilide chloride.

5. A fungicidal composition additionally possessing a plant growth-regulating action, which contains one or more N-alkyl-2,6-dimethylmorpholinocarboxamide salts of the formula I as claimed in claim 1 and an inert additive.

6. A method for controlling fungi, wherein one or more N-alkyl-2,6-dimethylmorpholinocarboxamide salts of the formula I as claimed in claim 1 are allowed to act on fungi or the articles to be protected from fungal infestation.

* * * * *

UNITED STATES PATENT AND TRADEMARK OFFICE
CERTIFICATE OF CORRECTION

PATENT NO. : 4,737,498
DATED : April 12, 1988
INVENTOR(S) : Lothar BANASIAK, et al.

It is certified that error appears in the above-identified patent and that said Letters Patent is hereby corrected as shown below:

Title page, item [73] should read:

Assignee: INSTITUT FUER PFLANZENSCHUTZFORSCHUNG KLEINMACHNOW DER AKADEMIE DER LANDWIRTSCHAFTSWISSENSCHAFTEN DER DDR, GERMAN DEMOCRATIC REPUBLIC and not as Assignee: BASF Aktiengesellschaft, Ludwigshafen, Fed. Rep. of Germany Signed and Sealed this Third Day of April, 1990

Attest:

HARRY F. MANBECK, JR.

Attesting Officer

Commissioner of Patents and Trademarks